United States Patent [19]
Ballard et al.

[11] 3,969,386
[45] July 13, 1976

[54] ORGANO-METALLIC COMPOUNDS

[75] Inventors: Denis George Harold Ballard; Adrian Walter Parkins; Peter Anthony Robinson; Samuel Dimewere Ibekwe, all of Runcorn; Michael Franz Lappert; Ronald Pearce, both of Brighton, all of England

[73] Assignee: Imperial Chemical Industries Limited, London, England

[22] Filed: Feb. 12, 1975

[21] Appl. No.: 549,303

Related U.S. Application Data

[63] Continuation of Ser. No. 311,520, Dec. 4, 1972, abandoned.

[30] Foreign Application Priority Data
Dec. 8, 1971 United Kingdom............... 56943/71
Dec. 8, 1971 United Kingdom............... 56944/71

[52] U.S. Cl.................... 260/429 R; 252/431 R; 260/429.3; 260/429.5; 260/438.5 R
[51] Int. Cl.².................. C07F 9/00; C07F 7/28; C07F 11/00
[58] Field of Search...... 260/429.3, 429 R, 438.5 R, 260/429.5

[56] References Cited
UNITED STATES PATENTS 3,763,197 10/1973 Collier et al..................... 260/429.3
3,813,423 5/1974 Pioli et al......................... 260/429.3

Primary Examiner—Helen M. S. Sneed
Attorney, Agent, or Firm—Cushman, Darby & Cushman

[57] ABSTRACT

Organometallic compounds of the general formula $L_rM(CH_2SiR^1R^2R^3)_m$ (1) where M is a transition metal of Groups IIIA to VIA of the Periodic Table of Elements, m is an integer from 1 to the prevailing valency of the metal M, $L_r$ represents the sum of any other incidental ligands attached to the metal M, r being 0 or an integer, and $R^1$, $R^2$ and $R^3$ represent substituted or unsubstituted hydrocarbyl groups or hydrogen atoms, at least one of said groups having the general formula $-(CH_2)_n Y$ (2) or 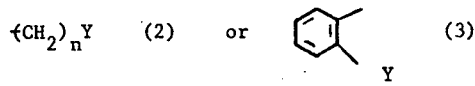 (3)

where $n$ is an integer from 1 to 5 and Y is a group capable of donating electrons to the metal M are useful as catalysts for olefin polymerization. The compounds may be used as catalysts alone or when supported upon a matrix for example of alumina. Particularly useful compounds are those in which the transition metal M has a valency lower than the maximum valency for that metal.

4 Claims, No Drawings

ORGANO-METALLIC COMPOUNDS

This is a continuation, of application Ser. No. 311,520 filed Dec. 4, 1972, now abandoned.

This invention relates to new organometallic compounds, to methods for their preparation and to the use of certain of these compounds as polymerisation catalysts.

According to one aspect of the present invention we provide, as new chemical compounds, organometallic compounds having the general formula:

$$L_rM(CH_2SiR^1R^2R^3)_m \qquad (1)$$

where M is a transition metal of Groups IIIA to VIA of the Periodic Table of Elments, m is an integer from 1 to the prevailing valency of the metal M, $L_r$ represents the sum of any other incidental ligands attached to the metal M, r being 0 or an integer, and $R^1$, $R^2$ and $R^3$ represent substituted or unsubstituted hydrocarbyl groups or hydrogen atoms, at least one of said groups having the general formula:-

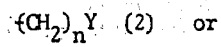 (2) or  (3)

where n is an integer from 1 to 5, and Y is a group capable of donating electrons to the metal M.

(All references to the Periodic Table are to the version of the Periodic Table of the Elements printed inside the back cover of "Advanced Inorganic Chemistry" by F A Cotton and G Wilkinson, 2nd Edition, Interscience Publishers, 1966).

Examples of suitable groups Y include aryl groups, which may be ring substituted, alkenyl groups, including allylic and cycloalkenyl groups, alkoxy groups, and phosphorus (III) containing groups. It is preferred that n has a vlaue of 1 or 2.

Hydrocarbyl groups $R^1$, $R^2$ and $R^3$ may be the same or different, provided that at least one has the formula:

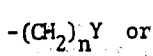 or 

Examples of suitable hydrocarbyl groups include alkyl, aryl, alkaryl and alkenyl groups and substituted derivatives thereof.

Incidental ligands L which may be neutral, cationic or anionic, are ligands which are present in order to satisfy the electronic and/or co-ordination requirements of the compounds. Thus it will be appreciated that they may be chosen from a wide range of ligands. Examples of such ligands include halide, alkoxide, carbonyl, cyclopentadienyl and ethers.

One preferred class of compounds according to formula (1) is that in which there are m similar ligands $(CH_2SiR^1R^2R^3)$ bound to metal M and $L_r$ is 0. Such compounds may be conveniently termed "isoleptic", that is, having only one type of ligand attached to the metal, i.e. in this case having the formula:

$$M(CH_2SiR^1R^2R^3)_m \qquad (4)$$

According to another aspect of the present invention, we provide, as new compounds, organometallic compounds of general formula (1) above in which the transition metal M has a valency lower than the maximum valency for that metal. Hereinafter such compounds will be referred to as "reduced valency organometallic compounds".

Examples of such compounds include the trivalent compounds of the metals of Groups IVA, the trivalent or quadrivalent compounds of the metals of Group VA and the divalent compounds of the metals of Group VIA, for example, compounds of titanium (III), vanadium (III), vanadium (IV), and chromium (II). Hitherto it has not proved possible to prepare such reduced valency isoleptic organometallic compounds in stable form at room temperature and, without prejudice to the invention, it is thought that it is the interaction of the group Y of the ligand–$(CH_2SiR^1R^2R^3)$ with the metal M which stabilises or at least contributes toward stabilisation of these reduced valency compounds.

The compounds of our invention may be useful as catalysts. In particular certain or our compounds, especially those of Group IVA to VIA metals are effective catalysts for the polymerisation and copolymerisation of olefinically unsaturated monomers, such as ethylene, propylene, butadiene and certain vinyl monomers. In particular trivalent titanium compounds may be useful as propylene polymerisation catalysts.

Compounds according to our invention may be conveniently prepared by means of a salt elimination reaction in accordance with the following general equation:

$$L_rMX_m + m(R^1R^2R^3SiCH_2M^1) \rightarrow$$
$$L_rM(CH_2SiR^1R^2R^3)_m + mM^1X \qquad (5)$$

where $M^1$ represents Li or MgX or another Main Group metal of Group I or metal radical of Group II or III, X represents a halogen and M, m, $R^1$, $R^2$ $R^3$ and $L_r$ have the significance given to them above.

The reaction may be most conveniently achieved using Grignard reagents, that is, as shown by the above equation when $M^1$ represents MgX. It is also preferred that the transition metal compound takes the form of a halide, as these are the most readily available compounds.

The reaction is preferably carried out in the liquid phase, the transition metal component being added to the Main Group I to III organometallic compound as a solution or suspension. Low reaction temperatures (0°C) are preferable and dry, oxygen-free conditions are essential. In some instances, for example, when preparing compounds in which the transition metal has a reduced valency, even lower temperatures (e.g. −50°C) may have to be used. Ether or hydrocarbon solvents may be used.

This reaction is particularly suited to the preparation of isoleptic compounds of formula (4), using the readily available transition metal halides, in accordance with equation (5), $L_r$ being 0. Should it be desired to prepare compounds including other ligands L, this may be conveniently accomplished by subjecting the isoleptic compounds to a further reaction to replace one or more of the ligands $(CH_2SiR^1R^2R^3)$ with one or more ligands L, for example, as shown by the following equation:

$$M(CH_2SiR^1R^2R^3)_m + nHX \rightarrow M(CH_2SiR^1R^2R^3)_{m-n}X_n + n\,CH_3SiR^1R^2R^3 \qquad (6)$$

where X represents a halogen atom.

Alternatively it may be possible in certain cases to add ligands L without elimination of any of the ligands $\{CH_2SiR^1R^2R^3\}$; for example a 2,2'-bipyridyl ligand may be added as shown in equation (7)

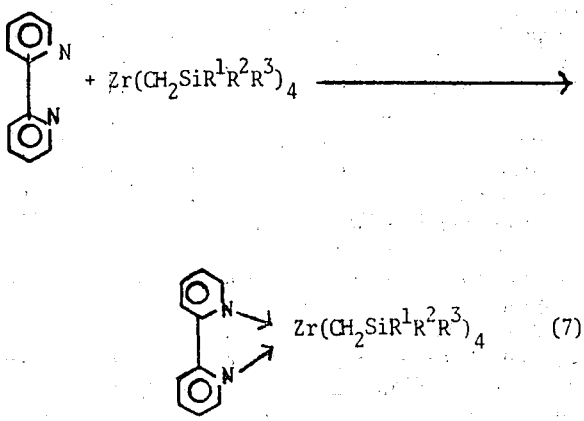

Such compounds, however, are generally inactive as polymerisation catalysts.

As has been previously mentioned, it is possible to prepare compounds according to formula (1) in which the transition metal M is in a valency state less than its maximum by incorporating one or more ligands $(CH_2SiR^1R^2R^3)$ in the compound. This may be accomplished by reacting a transition metal compound (preferably a halide) in which the metal is in the appropriate valency state with an appropriate organometallic compound of Main Group I to III metal according to equation (5).

In some instances, and especially when transition metals of Groups IVA and VA are used, very low reaction temperatures are desirable (e.g. $-50°C$) in order to avoid inadvertent decomposition of the product. However, once prepared, some of the products, for example, $Ti(CH_2SiMe_2CH_2Ph)_3$ and $Ti(CH_2SiMe_2CH_2CH=CH_2)_3$ may be stable at temperatures up to about 35°C. (Ph represents a phenyl group and Me represents a $CH_3$ group). In some instances disproportionation may occur during the reaction, so that the product comprises a mixture of compounds of two or more valency states of the transition metal. However, the presence of the reduced valency compound may be demonstrated in these instances, for example by electron spin resonance (e.s.r.) spectroscopy.

One especially convenient method of preparing the aforementioned reduced valency compounds is to replace the transition metal halide by an adduct of the halide with a suitable complexing agent so as to increase the solubility and hence the reactivity of the transition metal halide. Especially suitable complexing agents are labile Lewis bases, that is, Lewis bases which will form adducts with transition metal halides but whose basicity is not so great that the base may not be displaced by the ligand(s) $\{CH_2SiR^1R^2R^3\}$ in subsequent reaction, e.g. with a Grignard reagent.

Examples of labile Lewis bases include straight chain and cyclic ethers, amines, cyanides, ketones and sulphoxides. Preparation of adducts of transition metal halides with such complexing agents is readily accomplished, as described in J. Inorg. Nucl. Chem. 1962, 24 pp 1105 to 1109. The adducts of transition metal halides with tetrahydrofuran (THF) are particularly suitable.

Although the compounds of our invention are described and illustrated exclusively with respect to mono-metallic compounds, it will be appreciated that ligands $\{CH_2SiR^1R^2R^3\}$ may be bound to one transition metal and also interact with a second such metal, giving rise to di- or poly- metallic compounds.

Compounds according to our invention may be used to catalyse the polymerisation and copolymerisation of olefins, diolefins and some vinyl monomers. Within the term polymerisation we wish to include oligomerisation, that is, polymerisation to low molecular weight polymers. It will be appreciated that whether high molecular weight polymers or oligomers are produced will depend upon the combination of transition metal compound and monomer.

Polymerisation processes according to our invention may be carried out by techniques generally used for free radical initiated polymerisation or for polymerisation processes of the type using Ziegler catalysts. The choice of conditions of pressure and temperature will vary with factors such as the nature of the monomer and initiator, and whether bulk or diluent polymerisation is used. In general, however, it is preferred that the conditions are such that the olefin is present in a liquid phase.

The polymerisation activity of many of the compounds according to our invention may be enhanced by bonding them to a substantially inert matrix material having a hydroxylic surface, as described and claimed in our co-pending applications numbered 40416/69 and 40417/69 (UK) (equivalent to German O.L.S. No. 2040353). According to a further aspect of the invention, we provide a transition metal composition which is the product or reacting a transition metal complex of the general formula $L_rM(CH_2SiR^1R^2R^3)_m$ with a substantially inert matrix material having a hydroxylic surface (as hereinafter defined) which is free from absorbed water, wherein $L_r$, M, $R^1$, $R^2$, $R^3$ and $m$ are defined as above.

By a "hydroxylic surface" we mean a plurality of —OH groups attached to the surface of the matrix material, the hydrogen atom of the -OH group being capable of acting as a proton source, that is, having an acidic function. Such a material will be "substantially inert" in that, whereas the said —OH groups are capable of reacting with, say, the transition metal hydrocarbyl complex, the bulk of the matrix material is chemically inert. Particularly good examples of such matrix materials are silica and alumina or mixtures thereof. These comprise a matrix of silicon or aluminium and oxygen atoms, to the surface of which —OH groups are attached, the hydrogen atoms of said groups having an acidic function. However, apart from the presence of these —OH groups, silica and alumina are generally regarded as chemically inert. Within the terms silica and alumina we include silica and alumina based materials containing small amounts of other suitable inorganic oxides, such as magnesium oxide and zinc oxide.

It is essential that the matrix material is freed from adsorbed water, as this would merely react with and destroy the transition metal complex. The matrix materials may be readily freed from such adsorbed water by, for example, a simple thermal treatment.

The reaction between the appropriate transition metal complex and matrix material comprises displacement of one or more of the organosilicon ligands by the hydrogen atom of an —OH group or groups with liberation of the corresponding free organosilicon compound. The reaction may be represented by the following equation:

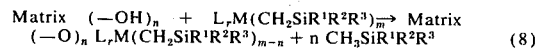
$$\text{Matrix} (-OH)_n + L_rM(CH_2SiR^1R^2R^3)_{\overline{m}} \rightarrow \text{Matrix} (-O)_n L_rM(CH_2SiR^1R^2R^3)_{m-n} + n\, CH_3SiR^1R^2R^3 \quad (8)$$

wherein $L_r$, M, $R^1$, $R^2$, $R^3$ and $m$ have the meanings previously ascribed to them and $n$ is an integer being not more than $(m-1)$. It has been found that when the matrix and the transition metal compound are reacted, all except one of the organosilicon groups of the transition metal compound may be displaced by —OH groups of the matrix, so that there is at least always one organosilicon group attached to the transition metal in the product. This appears to be independent of the number of reactable hydroxylic groups (as hereinafter defined) present on the surface of the matrix. The term Matrix $(-OH)_n$ represents an inert matrix having at least $n$ reactable hydroxylic groups attached to its surface. The number of reactable hydroxylic groups, that is, the number available for our reaction, will depend on the nature and condition of the matrix material. For example, in some materials, because of their molecular configuration, some of the hydroxylic groups present are not reactive under our conditions. Thus it is usual to react the matrix, at least initially, with an excess of transition metal complex, so that the number of hydroxylic groups available for the reaction may be determined.

The progress of the reaction in the manner indicated in equation (8) above may be readily followed by evolution of free organosilicon compound RH or by a colour change in the reactants.

As previously mentioned, the number of reactive hydroxylic groups present in a given weight of matrix will depend upon its nature (for example, wheather it is silica or alumina) and its condition (for example, its surface area and the treatment it has received to remove adsorbed water). Thus the precise composition of transition metal compositions according to our invention may vary from one batch or sample to another of the same matrix material; but successive portions of the same material prepared under identical conditions will give products having the same composition.

Compositions according to the present invention may be prepapred by contacting a solution of a transition metal complex with a suitable matrix material, in the absence of free or absorbed water. The solvent used for the complex should be dry and inert; hydrocarbon solvents are preferred. Since many of the transition metal complexes which may be used in our process are thermally unstable, the reaction temperature must be maintained low enough to avoid decomposition of the complex. With some complexes, temperatures below 0°C are required.

The ratio of organometallic complex to matrix material may be varied within wide limits depending upon the physical and chemical nature of the components used; but it is preferred that the proportions are chosen so that each reactable organosilicon group reacts with a hydroxylic group. Quantitative control over the ratio of organometallic complex to matrix material may be exercised by determining the amount of complex required to react fully with a given quantity of matrix. If the fully reacted matrix is not destroyed by the process of determination of its organometallic complex content, it may itself be used as a polymerisation catalyst. Alternatively a further quantity of organometallic complex may be added to another sample of the same batch of matrix material, either in the same ratio as that determined for the fully reacted matrix, in which case a second sample of fully reacted matrix material will be obtained, or in some lesser ratio, whereby a product can be obtained having a known percentage of the available hydroxylic groups reacted with the transition metal complex.

One method of determining the transition metal complex content of the fully reacted matrix is to isolate the product of reacting an excess of transition metal complex with a matrix material, destroying the matrix/transition metal complex composition for example with dilute hydrochloric acid and estimating the transition metal content of the acid solution by known analytical techniques.

A preferred method, which does not involve destruction of the product, comprises suspending the matrix material, which has previously been freed from water, in an inert liquid, adding an excess of the transition metal complex, and measuring the quantity of organosilicon compound produced for a given quantity of matrix material, for example by quantitative gas-liquid chromatography. A second sample of the matrix material is then taken and transition metal complex added until the quantity of organosilicon compound produced per gram of matrix material present is equivalent to, or a predetermined fraction of, that determined by addition of excess complex.

A further method which is preferred for reduced valency complexes, which are generally strongly coloured, but which may be used for any coloured complex, comprises suspending the dried matrix material in an inert liquid and titrating the reactable hydroxylic groups with a solution of a reduced valency transition metal complex in an inert solvent. The end point is readily detectable by the presence of a permanent colouration in the suspending solvent. The resultant products may then be recovered by filtration from the reaction medium, freed from solvent and stored dry or under solvent in oxygen-free conditions. Further samples of matrix material may then be reacted with calculated quantities of the transition metal complex to give fully or partially reacted products.

According to a further aspect of our invention, olefins are polymerised by means of an initiator which comprises a matrix-supported transition metal composition produced as hereinbefore described.

When our compounds are to be used for the polymerisation of propylene, the preferred matrix material is alumina, and the preferred transition metal complexes are titanium III complexes. The polymerisation process may be carried out under conditions commonly used to polymerise propylene; but the use of other conditions, e.g. high pressure, is not excluded. The reaction may be carried out in the liquid or gaseous phase. However, it is preferred that the propylene is used in liquid form and thus, if it is not liquid under the polymerisation conditions, it is preferably dissolved in a solvent. Examples of suitable solvents are aliphatic or aromatic hydrocarbons; for example, pentane, hexane, hepthane, octane, decane, benzene, toluene and mixtures thereof.

The polymerisation is preferably effected under an atmosphere free of oxygen, for example under an atmosphere of an inert gas, e.g. nitrogen, or of the monomer to be polymerised. It is also preferred to effect the process using apparatus and solvents which have been carefully freed from impurities, such as oxygen, water and other substances which would otherwise react with the initiators.

The temperature of polymerisation may vary over a wide range but is preferably in the range 20°–100°C.

The invention is further illustrated with reference to the following Examples:

EXAMPLE 1

Preparation of tetrakis(benzyldimethylsilylmethyl) titanium (IV), Ti(CH$_2$SiMe$_2$CH$_2$Ph)$_4$ PhCH$_2$SiMe$_2$CH$_2$Cl (12.04g., 0.061 mole) in ether (50 ml) was added to magnesium turnings (2g.) with stirring at a rate to maintain slow reflux. After the addition, the solution was heated to reflux for 1 hour, cooled, and freshly distilled 1,4-dioxan (5.36g., 0.061 mole) was added. The resulting white slurry was stirred for ½ hour and filtered to give a clear ethereal solution of the dialkylmagnesium reagent, which was estimated by a total base titration (yield : $2.075 \times 10^{-2}$ mole, 68%). Evaporation gave the dialkymagnesium reagent as a white solid which was slurried in dry hexane (100 ml.). To this slurry, at 0°C, was added TiCl$_4$ (2.07g., $1.09 \times 10^{-2}$ mole) in hexane (10 ml.) during 1½ hours with vigorous stirring. After stirring at 0°C for 16 hours the mixture was filtered to give a pale yellow filtrate which was evaporated to give Ti(CH$_2$SiMe$_2$CH$_2$Ph)$_4$ as a pale green-yellow liquid (yield : 4.80 g. = 66%). The compound was readily soluble in pentane from which pale yellow crystals were obtained on cooling to −70°C. Nmr (pentane) 2.8 (5H,m,Ar), 7.77 (4H, two overlapping S, TiCH$_2$Si and SiCH$_2$Ph), 9.68 (6H,s,SiMe$_2$) $\tau$ : ir 500 m (TiC$_4$) cm$^{-1}$. Hydrolysis of an aliquot gave benzyltrimethylsilane as the sole organic product (molar ratio PhCH$_2$SiMe$_3$:Zr = 3.95:1). On reaction with iodine the molar ratio of Zr:I$_2$ consumed was 1:4.20.

EXAMPLE 2

Preparation of tetrakis (benzyldimethylsilylmethyl)zirconium (IV) Zr(CH$_2$SiMe$_2$CH$_2$Ph)$_4$ The procedure of Example 1 was repeated using ZrCl$_4$ in place of TiCl$_4$. Evaporation of the filtrate gave rise to a pale yellow liquid comprising Zr(CH$_2$SiMe$_2$CH$_2$Ph)$_4$. Nmr (pentane 2.8 (5H,m,Ar), 7.76 (2H, s,SiCH$_2$Ph), 8.82 (2H, s,ZrCH$_2$Si), 9.70 (6H,s,SiMe) $\tau$; i.r. 470 m (ZrC4)cm$^{-1}$.

EXAMPLE 3

Preparation of tris(allyldimethylsilylmethyl)titanium (III)

Ti(CH$_2$SiMe$_2$CH$_2$CH=CH$_2$)$_3$

Allyldimethylsilylmethyl chloride (13g., 87 mmole) was slowly dropped on to magnesium turnings, (2g., 82mmole) in ether (30 ml.). After the reaction had started the remaining halide was diluted with ether (10 ml.) and further ether (30 ml.) added to the reaction flask. The reaction mixture was refluxed for 2 hours by warming on a water bath. Hydrogen reduced TiCl$_3$ was refluxed with an excess of tetrahydrofuran for 4 hours. The resultant mixture was allowed to cool to room temperature and the supernatant liquor decanted off, leaving a turquoise product (THF)$_3$ TiCl$_3$, which was dried in vacuo. The Grignard reagent solution was cooled to −50°C and solid (THF)$_3$TiCl$_3$ (9g., 34mmole) was added. The solution quickly darkened and was stirred at −50°C for 1½ hours and was then allowed to warm up to −5°C and left overnight. The solution was then filtered and the ether distilled off at room temperature. The dark residue was pumped at 10$^{-3}$ mm for 5 hours, extracted with pentane and the resulting dark solution filtered.

The pentane solution gave an e.s.r. spectrum (g=1.984) characteristic of paramagnetic titanium (III). The i.r. spectrum showed the complex to be free of both diethyl ether and tetrahydrofuran. A band at 1635 cm$^{-1}$ due to —CH=CH$_2$ was present.

Quantitative estimation of titanium (III) was carried out by an oxidimetric titration of the clear pentane solution using cerium (IV) sulphate as titrant and N-phenylanthranilic acid as indicator. A value of 35% titanium as Ti(III) was obtained.

EXAMPLE 4

Preparation of tetrakis(allyldimethylsilylmethyl)titanium (IV), Ti(CH$_2$SiMe$_2$CH$_2$CH=CH$_2$)$_4$ The procedure of Example 3 was repeated using TiCl$_4$ in place of the TiCl$_3$(THF)$_3$ adduct. Ti(CH$_2$SiMe$_2$CH$_2$CH=CH$_2$)$_4$ was obtained as a pale yellow compound soluble in pentane. It gave no e.s.r. signal, but its n.m.r. spectrum was not appreciably different from that of the paramagnetic titanium III analogue: n.m.r. of Ti(CH$_2$SiMe$_2$CH$_2$CH=CH)$_4$ 3.7–4.5 (1H,m,CH=CH$_2$), 4.9(1H,m,CH=CH$_2$), 5.1(1H,m,CH=CH$_2$), 7.60(2H,s,TiCH$_2$Si), 9.62(6H,s,SiMe$_2$) $\tau$; ir 500 m (TiC$_4$)cm$^{-1}$.

EXAMPLE 5

Preparation of tris(benzyldimethylsilylmethyl)titanium (III),

Ti(CH$_2$SiMe$_2$CH$_2$Ph)$_3$

The Grignard reagent PhCH$_2$Si Me$_2$CH$_2$MgCl was obtained by reacting PhCH$_2$SiMe$_2$CH$_2$Cl (19.9g., 100 mmoles) with magnesium turnings (excess) in sodium-dried diethyl ether (100 ml.). The reaction was started by adding a few drops of the pure halide on magnesium turnings in a little ether and warming. Once the reaction had started, it was maintained by adding the rest of the halide dissolved in ether at such a rate as to maintain a gentle reflux with vigorous stirring. Addition was carried out over a period of 1 hour and then the reaction mixture was refluxed for a further 2 hours to allow the reaction to go to completion.

The yield of Grignard reagent was about 88%. TiCl$_3$(5.2g., 34mmole) was added to the Grignard reagent, cooled to −30°C, over a period of 15 minutes with vigorous stirring. The reaction mixture was allowed to reach room temperature and stirring was continued for 4 hours, during which time the mixture turned dark brown.

The reaction mixture was then filtered on a G2 sinter and the ether completely removed at room temperature on a vacuum pump.

Th solid residue was extracted with dry pentane at room temperature and filtered on a G4 sinter. The clear filtrate was a yellowish-brown in colour, and gave a strong e.s.r. spectrum (g. = 1.990), characteristic of titanium (III).

EXAMPLE 6

Preparation of tris(allyldimethylsilylmethyl)vanadium (III)

V(CH$_2$SiMe$_2$CH$_2$CH=CH$_2$)$_3$

VCl$_3$ was refluxed with an excess of tetrahydrofuran for 4 hours. The resultant mixture was allowed to cool to room temperature and the supernatant liquor decanted off, leaving a pink product, VCl$_3$(THF)$_3$ (12.5 g., 34 mmole), which was added to the Grignard reagent at −40°C. Reaction occured immediately and a dark-green solution resulted. The organometallic vanadium compound so obtained was isolated as described for the equivalent titanium compound.

EXAMPLE 7

Preparation of tetrakis(benzyldimethylsilylmethyl) vanadium (IV)

V(CH$_2$SiMe$_2$CH$_2$Ph)$_4$

The Grignard reagent PhCH$_2$SiMe$_2$CH$_2$MgCl was prepared as described in Example 5 from 100 mmoles of the halide and VCl$_4$ (6.5g, 34 mmole) was added to the reagent, cooled to −30°C, over a period of 15 minutes with vigorous stirring. The reaction mixture was allowed to reach room temperature and stirring was continued for 4 hours. The reaction mixture was filtered and the ether removed under vacuum, giving a solid residue which was dissolved in heptane to give an emerald green solution.

EXAMPLE 8

Preparation of bis(allyldimethylsilylmethyl) chromium (II),

Cr(CH$_2$SiMe$_2$CH$_2$CH=CH$_2$)$_2$

The Grignard reagent CH$_2$=CH CH$_2$Me$_2$SiCH$_2$MgCl was prepared as described in Example 3, and to 18 mmole of the Grignard reagent was added 11 mmole of CrCl$_2$ 2THF at −30°C. The initial sandy brown colour of the chromium complex turned to blue-green, and after stripping the ether and THF under vacuum, the black residue was dissolved in heptane to give a bright purple solution.

E.s.r. spectroscopy showed a weak signal characteristic of paramagnetic chromium II.

Analysis of the solution showed 2.43 mg Cr/5ml, compared with 0.67mg Mg/5ml of 0.0mg Cl/5ml.

EXAMPLE 9

Preparation of tris(o-methoxyphenyldimethylsilylmethyl)scandium (III)

Sc(CH$_2$SiMe$_2$ o-MeOC$_6$H$_4$)$_3$

The lithium compound o-MeOC$_6$H$_4$SiMe$_2$CH$_2$Li was prepared by adding bromomethyldimethyl(o-methoxyphenyl)silane (0.1 mole) dropwise over 6 hours to a dispersion of lithium powder (0.6 mole) in hexane (200 ml) and ether (40 ml) at 50°C. The mixture was filtered and the filtrate evaporated to approx. 50 ml and cooled to −30°C whereupon the lithium compound separated as a white solid which was separated and redissolved in hexane/ether (5:1 v/v) to give a 0.25M solution, estimated by total base titration.

A volume of the above solution containing 14.7 mmole of the reagent was added to ScCl$_3$.3THF (1.63g., 4.44 mmole) at −50°C.

The slurry was warmed to room temperature and stirred for 2 hours. The supernatant liquid was removed by filtration and the white residue extracted with methylene chloride (15 ml). Filtration gave a pale yellow filtrate which was evaporated to give the crude product as a yellow solid (2.47g, 95%). Crystallisation from methylene chloride/pentane (2:1) gave tris(o-methoxyphenyldimethyl-sily-lmethyl)scandium (III) m.p. 115°–120° (dec.); nmr (C$_6$H$_6$) 2.5 – 3.1 (4H,m, Ar), 6.14 (3H, s, OMe), 9.45 (6H, s, SiMe$_2$), 9.92 (2H,s,SiCH$_2$Sc)$\tau$ ; ir 480m, br (Sc-C)cm$^{-1}$. (Found: C, 61.4; H, 7.64; Si, 14.2; Sc, 7.51. C$_{30}$H$_{45}$O$_3$Si$_3$Sc requires C, 61.8; H, 7.78; Si, 14.5; Sc, 7.71%).

EXAMPLE 10

Preparation of tetrakis(o-methoxyphenyldimethylsilylmethyl)zirconium (IV)

Zr(CH$_2$SiMe$_2$o-MeOC$_6$H$_4$)$_4$

To a solution of o-methoxyphenyldimethylsilylmethylmagnesium chloride, prepared from chloromethyldimethyl(o-methoxyphenyl) silane (30.0 g, 140 mmole) and magnesium (4.0g, 0.164 gatom) in ether (250 ml), was added zirconium tetrachloride (8.15g., 35 mmole) portionwise over 1 hour. The mixture was stirred at room temperature (with rough exclusion of light) for 20 hours and then filtered. The filtrate was evaporated to a brown oil (26.4g, 94% of crude product). This was dissolved in hexane (75 ml) and filtered to remove traces of undissolved solid to give a deep orange solution of the zirconium compound. Hydrolysis of an aliquot gave o-methoxyphenyltrimethylsilane as the sole organic product (molar ratio o- MeOC$_6$H$_4$SiMe$_3$:Zr=3.98:1). Nmr (C$_6$H$_6$) 2.5-3.4 (4H,m,Ar), 6.48 (3H,s,OMe), 8.70 (2H,s,CH$_2$Si), 9.42 (6H,s,SiMe$_2$)$\tau$ ; ir 475 m,br (Zr-C$_4$)cm$^{-1}$.

Similarly, a hexane solution of the zirconium compound was obtained by reaction of zirconium tetrachloride (4.60g, 19.7 mmole) with o-methoxyphenyldimethylsilylmethyl lithium (75 mmole) in ether (120 ml.).

EXAMPLE 11

Preparation of tetrakis(allyldimethylsilylmethyl)zirconium (IV)

Zr(CH$_2$SiMe$_2$CH$_2$CH=CH$_2$)$_4$

The above compound was prepared as in Example 3, using ZrCl$_4$ in place of the TiCl$_3$. 3THF complex, and was obtained as a pale yellow solution in heptane.

EXAMPLE 12

Preparation of tris(4-but-1-enyldimethylsilylmethyl)titanium (III)

Ti(CH$_2$SiMe$_2$CH$_2$CH$_2$CH=CH$_2$)$_3$ 4-but-1-enyldimethylsilylmethylchloride (7.7g) was reacted with 1.2g Mg to give the corresponding Grignard reagent. A solution of 44 mmole of the Grignard reagent in ether was cooled to −40°C and treated with 5.4g (14.7 mmoles) of TiCl$_3$.3THF in ether. The solution was allowed to warm to −10°C and filtered. The ether was removed under vacuum at −30°C and the residue extracted with pentane to give a clear brown solution. E.s.r. of the solution showed a signal at g = 1.98, characteristic of paramagnetic titanium (III).

EXAMPLE 13

Preparation of
bis(o-methoxyphenyldimethylsilylmethyl)bis-(acetylacetonato) zirconium (IV)
(o-MeOC$_6$H$_4$Me$_2$SiCH$_2$ )$_2$ Zr (acac)$_2$ To a solution of tetrakis (o-methoxyphenyldimethylsilylmethyl) zirconium (IV) (10 mmole) in hexane, prepared as in Example 10, was added dropwise at −78° a solution of acetylacetone in hexane (20 mmole) over a period of 2 hours. The solution was allowed to warm to room temperature, volatile material removed under vacuum, and the resulting crude product obtained as a yellow liquid.

EXAMPLES 14–18

Polymerisation of olefins by unsupported transition metal complexes

A 1 liter stainless steel stirred autoclave was carefully dried and all oxygen was removed. 500 ml. of n-heptane were added and a solution of the complex introduced, the autoclave heated to 60°C and ethylene introduced until the pressure was 100 p.s.i.g. The reaction pressure was maintained by the addition of ethylene and the reaction temperature controlled by cooling. After the stated time the pressure was released, the autoclave contents cooled and the product polyethylene was freed from the solvent.

Propylene was polymerised in the same manner at a temperature of 65°C, to yield a product consisting of soluble and insoluble polypropylene, the two fractions being separated by filtration.

The results are shown in Table 1.

Preparation of Transition Metal/Matrix Composition

A sample of γ-alumina (surface area ~100 sq.m. per g.) was heated for 2 hours in a furnace at T°C (actual temperature shown in Table 2) in an atmosphere of dry, oxygen-free nitrogen, allowed to cool under the atmosphere of nitrogen and finally suspended in dry, oxygenfree toluene. The suspension was then titrated with a solution of the appropriate transition metal complex dissolved in toluene, the endpoint being indicated by a permanent colour in the suspending solvent. (For example 0.33 mM of Ti(CH$_2$SiMe$_2$CH$_2$CH=CH$_2$)$_3$ were required for 1g. support). At the end of the titration the colour of the complex was discharged from the toluene and a coloured composition was obtained.

Polymerisation of Propylene

A 1 liter stainless steel stirred autoclave was carefully dried and all oxygen was removed. 500 ml. of n-heptane were added and a suspension of the appropriate transition metal composition was introduced, the autoclave was heated to 65°C and propylene was introduced until the pressure was 100 p.s.i.g. The reaction pressure was maintained by the addition of propylene and the temperature controlled by cooling. After the stated time (see Table 2) the pressure was released, the autoclave and contents cooled and polypropylene recovered from the reaction mixture. The reaction products consisted of soluble and insoluble polypropylene, the two fractions being separated by filtration.

The results are set out in Table 2 below.

TABLE 2

| Example No. | Transition Metal Complex | Matrix Pre-Treatment Temperature T°C | Catalyst added (mM of complex) | Polymerisation Time (hrs) | Yield (g) | Activity (g/mM/atm/hr) | % Insoluble Polypropylene |
|---|---|---|---|---|---|---|---|
| 19 | Ti(CH$_2$SiMe$_2$CH$_2$CH=CH$_2$)$_3$ | 500 | 0.8 | 2.0 | 13.0 | 1.1 | 88 |
| 20 | Ti(CH$_2$SiMe$_2$CH$_2$CH=CH$_2$)$_3$ | 350 | 0.6 | 1.0 | 1.3 | 0.3 | 31 |
| 21 | Ti(CH$_2$SiMe$_2$CH$_2$Ph)$_3$ | 500 | 1.1 | 1.0 | 10.8 | 1.4 | 61 |
| 22 | Ti(CH$_2$SiMe$_2$CH$_2$Ph)$_3$ | 750 | 0.7 | 2.0 | 1.4 | 0.14 | 57 |
| 23 | Ti(CH$_2$SiMe$_2$CH$_2$Ph)$_4$ | 350 | 0.4 | 1.0 | 10.7 | 4.0 | 52 |
| 24 | Ti(CH$_2$SiMe$_2$CH$_2$Ph)$_4$ | 500 | 0.5 | 1.0 | 35.7 | 10.7 | 59 |
| 25 | Zr(CH$_2$SiMe$_2$oMeOC$_6$H$_4$)$_4$ | 500 | 0.5 | 1.0 | 2.2 | 0.66 | 79 |
| 26 | Zr(CH$_2$SiMe$_2$oMeOC$_6$H$_4$)$_4$ | 350 | 0.5 | 1.5 | 1.4 | 0.27 | 72 |
| 27 | V(CH$_2$SiMe$_2$CH$_2$Ph)$_3$ | 500 | 1.5 | 1.5 | 1.3 | 0.08 | 0 |
| 28 | Zr(CH$_2$SiMe$_2$CH$_2$CH=CH$_2$)$_4$ | 350 | 0.5 | 1.5 | 0.8 | 0.2 | 50 |
| 29 | Zr(CH$_2$SiMe$_2$CH$_2$CH=CH$_2$)$_4$ | 500 | 0.7 | 1.5 | 1.8 | 0.3 | 78 |
| 30 | Ti(CH$_2$SiMeCH$_2$CH$_2$CH=CH$_2$)$_3$ | 500 | 0.45 | 1.5 | 0.8 | 0.25 | 0 |

EXAMPLE 31

Polymerisation of ethylene by supported transition metal complexes

Ethylene was polymerised as described in Examples 14-18, using as catalyst Zr(CH$_2$SiMe$_2$CH$_2$CH=CH$_2$)$_4$ supported on alumina previously treated at 500°C.

| Example No. | Transition metal complex | Monomer | Complex Added (mM) | Time hrs. | Yield (g) | Activity (g/mM/atom/hr) |
|---|---|---|---|---|---|---|
| 14 | Ti(CH$_2$SiMe$_2$C$_3$H$_5$)$_3$ | C$_2$H$_4$ | 1.5 | 4 | 2.8 | .07 |
| 15 | Ti(CH$_2$SiMe$_2$CH$_2$C$_6$H$_5$)$_4$ | C$_2$H$_4$ | 1.5 | 4 | 14 | .35 |
| 16 | Ti(CH$_2$SiMe$_2$C$_3$H$_5$)$_3$ | C$_3$H$_6$ | 5 | 64 | 0.2 | 10$^{-4}$ |
| 17 | Ti(CH$_2$SiMe$_2$C$_3$H$_5$)$_3$ | C$_3$H$_6$ | 5 | 42 | 0.9 | 6.10$^{-4}$ |
| 18 | Ti(CH$_2$SiMe$_2$CH$_2$C$_6$H$_5$)$_4$ | C$_3$H$_6$ | 5 | 64 | 1.6 | 8.10$^{-4}$ |

EXAMPLES 19–30

Polymerisation of propylene by supported transition metal complexes

Using 0.1 mM of supported Zr complex and a reaction time of 2 hr., the yield obtained was 71g of polyethylene, corresponding to an activity of 142 g/mM/atm/hr.

What we claim is:

1. An organometallic compound of the formula $$M(CH_2SiR^1R^2R^3)_m$$

where M is selected from transition metals of Groups IIIA to VIA of the Periodic Table of Elements, $m$ is the prevailing valency of the metal M, said prevailing valency being 2, 3 or 4, and $R^1$, $R^2$ and $R^3$ are selected from hydrogen, alkyl, alkenyl, benzyl and alkoxyphenyl, at least one of $R^1$, $R^2$ and $R^3$ being alkenyl, benzyl or alkoxyphenyl.

2. A compound as claimed in claim 1 in which at least one of said groups $R^1$, $R^2$ and $R^3$ is selected from allyl, benzyl and o-methoxy-phenyl groups and any remaining $R^1$, $R^2$ and $R^3$ groups are methyl.

3. A compound as claimed in claim 1 wherein the alkenyl contains up to 4 carbon atoms.

4. Compounds as claimed in claim 1 in which said transition metal M is selected from titanium, vanadium and chromium.

* * * * *